(12) United States Patent
Zell

(10) Patent No.: US 6,625,829 B2
(45) Date of Patent: Sep. 30, 2003

(54) CHIN SUPPORT PILLOW

(76) Inventor: Kenneth D. Zell, 25912 Hayward Blvd., #312, Hayward, CA (US) 94542-1649

( * ) Notice: Subject to any disclaimer, the term of this patent is extended or adjusted under 35 U.S.C. 154(b) by 45 days.

(21) Appl. No.: 09/940,163

(22) Filed: Aug. 27, 2001

(65) Prior Publication Data

US 2003/0037376 A1 Feb. 27, 2003

(51) Int. Cl.[7] ................................................ A61F 5/055
(52) U.S. Cl. ................................ 5/637; 5/636; 602/18; 128/DIG. 23
(58) Field of Search ............................. 5/636, 637, 638, 5/639, 640, 641–645; 602/18; 128/DIG. 23

(56) References Cited

U.S. PATENT DOCUMENTS

| | | |
|---|---|---|
| 2,336,707 A | 12/1943 | Thompson |
| 3,327,330 A | 6/1967 | McCullough |
| 3,477,425 A | 11/1969 | Grassl |
| 4,236,264 A | 12/1980 | Britzman |
| 4,617,691 A | 10/1986 | Monti et al. |
| 4,776,049 A | 10/1988 | Perron |
| 6,219,865 B1 | 4/2001 | Stokesbary |
| 6,231,535 B1 | 5/2001 | Mainiero et al. |

Primary Examiner—Heather Shackelford
Assistant Examiner—Frederick Lyndon Lagman
(74) Attorney, Agent, or Firm—Harris Zimmerman

(57) ABSTRACT

A chin support pillow for supporting a person's head in an upright position while sitting. The pillow includes an elongate cushioning body with a cloth covered foam core and a zippered cloth outer cover. A flexible strap extends from one end of the body and is connectable to the other end of the body using interconnecting patches of hook and loop fastener material to bend the body at the center into a V-shaped configuration. The center of the body in such a V-shaped configuration fits between the chin and the upper chest region of the person with the first and second legs extending along and fitting between opposite lower edges of the jaw and the respective shoulder regions to support the person's head. The flexible member extends around the back of the person's neck and is of adjustable length to custom fit the person wearing the chin support pillow.

5 Claims, 2 Drawing Sheets

1

CHIN SUPPORT PILLOW

BACKGROUND OF THE INVENTION

1. Field of Invention

The present invention relates generally to head and neck support devices and more particularly to non-medical type support devices for providing forward and lateral support to the head and neck while in a sitting position or a prone position.

2. Description of Related Art

Many types of head and neck support devices have been developed over the years, of both the medical and non-medical types.

Medical Type Head and Neck Support Devices

The medical type head and neck support devices are designed to prevent injury or further injury to the person. One typical device comprises a cervical collar made of rigid or semi-rigid plastic which is affixed around the neck of accident victims. The collar abuts the jaw, collar bone, and shoulders to retain the head and neck from forward, rearward, and lateral movement to prevent further injury to the spine when transporting the accident victim from the scene of the wreck to the hospital. Other similar devices are used to treat persons whom have had recent spinal surgery until sufficient healing has taken place, to treatment of whiplash victims from car accidents, and for persons having debilitating injuries such as paralysis, wherein permanent support for the head and neck is required.

Non-Medical Type Head and Neck Support Devices

Non-medical type head and neck support devices are typically used to enhance the comfort of the user rather than as treatment or for injury prevention. For example, when a person is sitting in an upright position such as during reading, supporting of the head and neck from tipping forward can provide increased comfort over using one's neck muscles.

One example is disclosed in U.S. Pat. No. 3,327,330 issued to McCullough, which is a comfort pillow for protecting hair stylings while sleeping, and which also provides firm support to a user's neck and back for therapeutic purposes. The pillow comprises an L-shaped main body of cloth filled with dacron polyester fibers. The body includes respective first and second legs which extend angled outwardly for an equal distance. A respective wing is articulately connected at the distal end of each leg, each wing having half of a fastening device which mate together whereby the wings can be folded back on the main body and joined. The folded position increases the effective height of the pillow for additional user comfort.

Another example is disclosed in U.S. Pat. No. 6,231,535 issued to Mainiero et al. which is a support for maintaining the head of a user erect when in a sitting position such as while in an airplane. The support includes a rigid body which fits below the chin of the user. The body includes a plurality of arcuately-shaped surfaces contoured to accommodate the clavicle, the chin, the upper chest, and the neck of the user, and the knot of a tie if worn by the user. A strap that extends from opposite ends of the body for engaging around the neck of the user.

Yet another example is disclosed in U.S. Pat. No. 6,219,865 issued to Stokesbary which is a head support comprising a resilient wedge which fits below the user's chin with respective integrally molded tapered straps which wrap around opposite sides of the user's neck. The straps removably connect together for maintaining the wedge in the position under the user's chin. A removable washable cover is disposed over the wedge.

Other examples of support pillows include that disclosed in U.S. Pat. No. 2,336,707 issued to Thompson, comprising a generally U-shaped pillow having a compressible center portion at the bottom of the "U". Opposite ends of the center portion are connected to a pair of relatively large and incompressible side portions forming a neck receiving hole. In U.S. Pat. No. 4,617,691 issued to Monti et al. is disclosed a pillow of generally rectangular shape with a circular opening therein adapted to encircle the user's neck while resting on the user's shoulders. Finally, in U.S. Pat. No. 4,236,264 issued to Britzman is disclosed a pillow having an inflatable horseshoe shaped body with respective legs projecting from the bottom of the horseshoe. The free ends of the legs are urged inwardly toward one another upon filling of the body with pressurized air to grip the opposite sides of the user's neck or other body part to which the pillow is applied.

While the above mentioned head and neck support devices provide various benefits to the users thereof, none are of simple cloth and polyester foam design which comfortably support the head and neck of the user while in an upright sitting position as well as in a prone or reclining position.

SUMMARY OF INVENTION

1. ADVANTAGES OF THE INVENTION

One of the advantages of the present invention is that it provides a chin support pillow which supports the head and neck of the user while in an upright sitting position as well as in a prone or reclining position.

Another advantage of the present invention is its construction of cloth and polyester foam which is extremely comfortable.

A further advantage of the present invention is its inexpensive yet durable construction which lends itself to disposable use such as on airlines and buses.

Yet another advantage of the present invention is its removable outer cover which can be laundered separately from the cushioning core.

A still further advantage of the present invention is the ability to use a flexible plastic material for the inner cover, which is heat sealed around the polyester foam core to provide a core which is sealed from the ingress of sweat and other such liquids, and which can be disinfected for later reuse.

These and other advantages of the present invention may be realized by reference to the remaining portions of the specification, claims, and abstract.

2. BRIEF DESCRIPTION OF THE INVENTION

The present invention comprises a chin support pillow to support the head of a person from tilting forward. The chin support pillow includes an elongate cushioning body which is foldable at a center thereof to form a generally V-shaped configuration. The body has respective first and second legs which extend from said center and which terminate at respective first and second end portions. The chin support pillow further includes an elongate flexible member having respective opposing first and second end portions which are connectable to the respective end portions of the first and second legs. The center of the body in the V-shaped configuration fits between a chin and an upper chest region of the person. The first and second legs extend along and fit between opposite lower edges of the jaw and respective shoulder regions of the person to support the head. The strap extends rearwardly around the head and neck to retain the chin support pillow in position.

The above description sets forth, rather broadly, the more important features of the present invention so that the detailed description of the preferred embodiment that follows may be better understood and contributions of the present invention to the art may be better appreciated. There are, of course, additional features of the invention that will be described below and will form the subject matter of claims. In this respect, before explaining at least one preferred embodiment of the invention in detail, it is to be understood that the invention is not limited in its application to the details of the construction and to the arrangement of the components set forth in the following description or as illustrated in the drawings. The invention is capable of other embodiments and of being practiced and carried out in various ways. Also, it is to be understood that the phraseology and terminology employed herein are for the purpose of description and should not be regarded as limiting.

BRIEF DESCRIPTION OF THE DRAWINGS

Preferred embodiments of the present invention are shown in the accompanying drawings wherein.

DESCRIPTION OF THE PREFERRED EMBODIMENT

Figure 1:
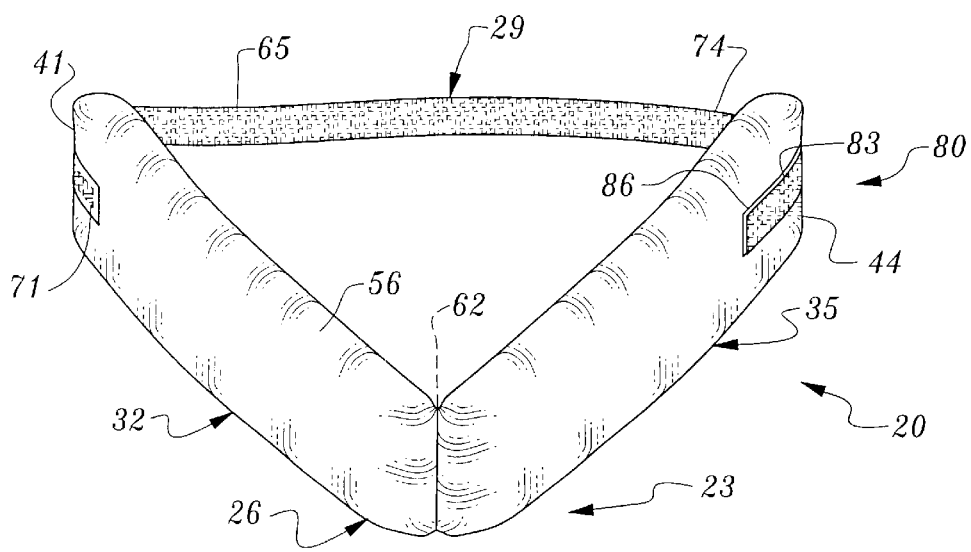
FIG. 1 is substantially a front perspective view of a chin support pillow according to the present invention shown in a V-shaped folded position.
Figure 2:
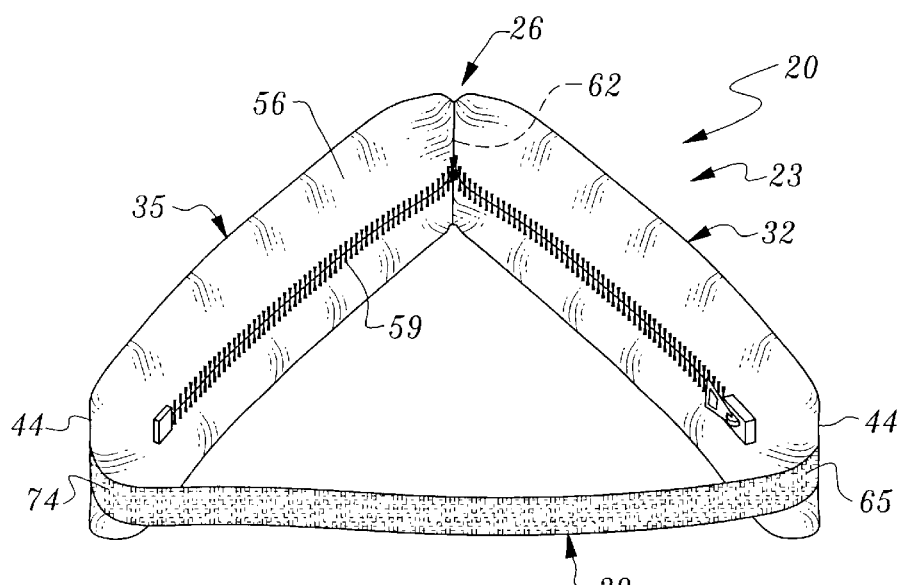
FIG. 2 is substantially a rear perspective view of the chin support pillow corresponding to FIG. 1.
Figure 3:
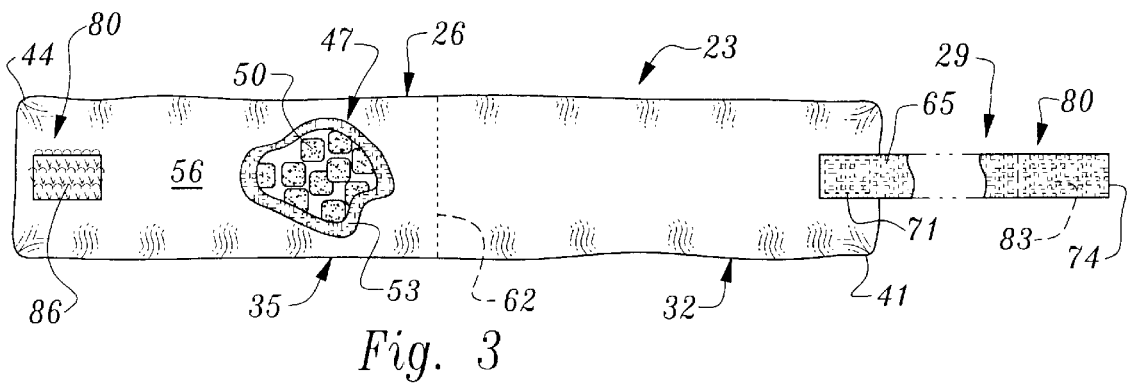
FIG. 3 is substantially a front elevational view of the chin support pillow in an unfolded position.

As seen in FIGS. 1–3, the present invention comprises a chin support pillow, generally indicated by reference number 20. The chin support pillow 20 is comprised of an elongate body 23 of cushioning configuration which is foldable at a center 26 thereof to form a generally V-shaped configuration as shown. The chin support pillow 20 is retainable in such configuration by an elongate flexible member in the form of a strap 29.

The body 23 includes first and second legs 32 and 35 which extend in opposite directions from the center 26 of the body 23. The legs 32 and 35 terminate at respective end portions 41 and 44. The body 23 includes a foam core 47 made of a plurality of individual foam chunks 50 of cushioning polyester foam contained within a sewn plastic or cloth inner cover 53 similar to a standard pillow. The body further includes a sewn plastic or cloth outer cover 56 similar to a standard pillow cover, having a zipper 59 sewn longitudinally therealong to permit the foam core 47 to be inserted and removed. A sewn seam 62 extends transversely across the foam core 47 at the center 26 of body 23.

The strap 29 includes a first end portion 65 which is affixed to the end portion 41 of the first leg 32. More specifically, the first end portion 65 is affixed to the outer cover 56 at a sewn seam 71. A second end portion 74 of the strap 29 is removably connectable to the end portion 44 of the second leg 35 using a connecting device 80 comprising respective mating hook and loop patches 83 and 86. The hook patch 83 is affixed to the second end portion 74 such as by sewing. The loop patch 86 is affixed to the end portion 77 of the second leg 35 such as by sewing. Patches 83 and 86, one version of which are known in the industry by the trade name VELCRO, are overlapped a desired amount and pressed together to removably retain the second end portion 74 of the strap 29 to the end portion 77 of the second leg 35. Lifting the second end portion 74 with the hook patch 83 away from the end portion 77 with the loop patch 86 disconnects the respective hook and loop patches 83 and 86.

Figure 4:
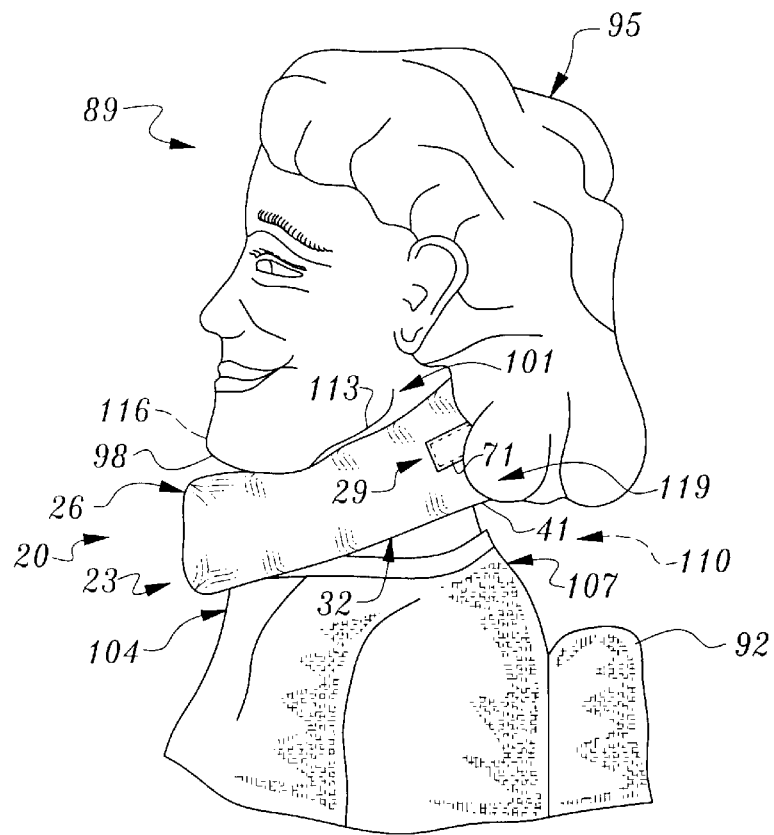
FIG. 4 is substantially a side elevational view of the chin support pillow as worn by a person sitting in an upright position.
Figure 5:
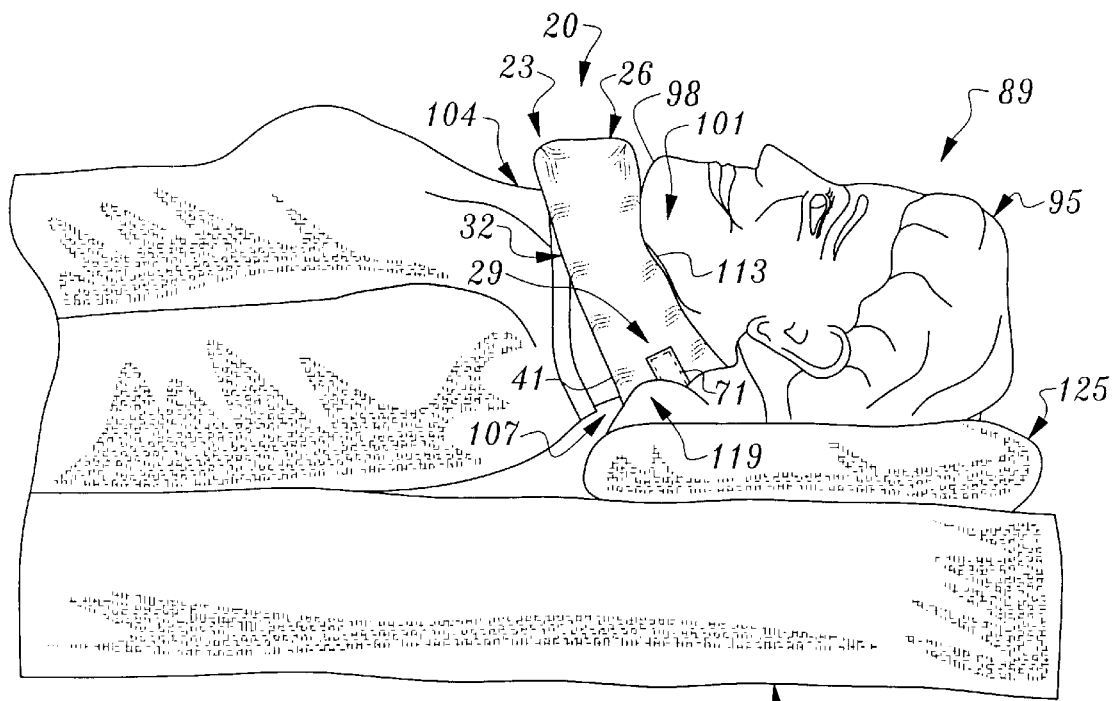
FIG. 5 is substantially a side elevational view corresponding to FIG. 5, but with the person in a prone position.

Referring to FIGS. 4 and 5, therein is shown the chin support pillow 20 as used by a person 89. The person 89 in FIG. 4 is shown sitting upright as supported by a chair, the backrest 92 being visible. The chin support pillow 20 supports the head 95 of the person 89 in an upright position by supporting the person's chin 98 and jaw 101 against the upper chest 104 and respective left and right shoulder regions 107 and 110 of the person. The center 26 of the body 23, when in the V-shaped configuration as shown, fits between the person's chin 98 and upper chest 104. The first and second legs 32 and 35 extend along and fit between opposite lower edges 113 and 116 of the person's jaw 101 and the person's respective shoulder regions 107 and 110 to support the person's head 95. The strap 29 extends rearwardly around the person's head 95 and neck 119 to retain the chin support pillow 20 in the V-shaped configuration under the person's chin 98 and jaw 101.

In FIG. 5, the person 89 is shown in a prone position as supported by a bed, the mattress 122 being visible, along with a standard pillow 125 positioned below the person's head 95. The pillow 125 tends to pivot the person's head 95 and neck 119 upwardly and toward the person's upper chest 104, which can be uncomfortable. The chin support pillow 20 operates in the manner explained above for the vertical position, by supporting the person's chin 98 and jaw 101 against the upper chest 104 and respective left and right shoulder regions 107 and 110. The chin support pillow 20 thus supports the person's head 95 in a more horizontal position which is more comfortable for person 98 than without the chin support pillow 20.

CONCLUSION

It can now be seen that the present invention solves many of the problems associated with the prior art. The present invention provides a chin support pillow which supports the head and neck of the user while in an upright sitting position as well as in a prone or reclining position. The present invention further provides a chin support pillow which is of a construction of cloth and polyester foam which is extremely comfortable. The present invention further provides a chin support pillow which is its inexpensive yet durable construction which lends itself to disposable use such as on airlines and buses. The present invention still further provides a a chin support pillow which has a removable outer cover which can be laundered separately from the cushioning core. The present invention yet further provides a chin support pillow which has the ability to use a flexible plastic material for the inner cover, which is heat sealed around the polyester foam core to provide a core which is sealed from the ingress of sweat and other such liquids, and which can be disinfected for later reuse.

Although the description above contains many specifications, these should not be construed as limiting the scope of the invention but as merely providing illustrations of some of presently preferred embodiments of this invention. The specification, for instance, makes reference to the inner and outer covers being made of cloth. However, the present invention is not intended to be limited to cloth. Rather it is intended that the present invention can be made using a thin flexible plastic or other such material. Likewise, while the sewn seams are referred to, the present invention can use other types of seams such as heat sealed seams such as when plastic is used rather than cloth. Plastic coated cloth can also be used. If reuseablity and/or disposability is desired, any of the well-known disposable cloth or paper materials such as that used to cover airline pillows can be used either as the outer and/or inner covers, or as a separate exterior cover over the outer cover. While polyester foam is preferably used in the core, other cushioning materials known for use in pillows, insulated clothing, and other such articles can be used. Finally, while a single strap and a connecting device in the form of interlocking patches of hook and loop material are disclosed for retaining the chin support pillow to the user, other ways are possible. For example, a pair of elongate cloth ties can be affixed at one end to the end of each of the first and second legs, the opposite ends of which ties can be brought together and tied in a knot to retain the chin support pillow to the user. Thus, the scope of the invention should be determined by the appended claims and their legal equivalents rather than by the examples given.

Terms 20. chin support pillow
23. [pillow] elongate body
26. [body] center
29. [pillow] strap
32. [body] first leg
35. [body] second leg
41. [first leg] end portion
44. [second leg] end portion
47. [body] foam core
50. [foam core] foam chunk
53. [foam core] inner cover
56. [body] outer cover
59. [outer cover] zipper
62. [foam core] seam
65. [strap] first end portion
71. [outer cover] seam
74. [strap] second end portion
80. [pillow] connecting device
83. [connecting device] hook patch
86. [connecting device] loop patch
89. person
92. chair backrest
95. [person] head
98. [person] chin
101. [person] jaw
104. [person] upper chest
107. [person] left shoulder region
110. [person] right shoulder region
113. [jaw] lower edge
116. [jaw] lower edge
119. [person] neck
122. bed mattress
125. standard pillow

What is claimed is:

1. A chin support pillow to support the head of a person from tilting forward and sideways, comprising:

an elongate cushioning body which is foldable at a center thereof to form a generally V-shaped configuration comprising respective first and second legs which extend from said center and which terminate at respective first and second end portions; said body comprising a flexible outer cover surrounding a cushioning core;

an elongated flexible member having respecting opposing first and second end portions which are connectable to the respective end portions of said first and second legs;

said center of said body in said V-shaped configuration fits between a chin and an upper chest region of the person with said first and second legs extending along and fitting between opposite lower edges of a jaw and respective shoulder regions of the person to support the head, said strap which extends rearwardly around the head and neck to retain the chin support pillow in position; wherein the center of the body is sewn together at a transverse seam which facilitates folding of said body at said seam; and wherein the body further comprises an inner cover which surrounds the cushioning core, and wherein the outer cover is decorative; and wherein a center of the inner cover is sewn together at a transverse seam which facilitates folding of the body at said seam.

2. The pillow of claim 1, wherein said core comprises a plurality of individual chunks of foam; and wherein a center of the inner cover is sewn together at a transverse seam which facilitates folding of the body at said seam, and wherein said body includes a zipper which is affixed to the outer cover longitudinally thereof which permits access to said inner cover disposed within said out cover.

3. The pillow of claim 2, wherein the flexible member is of adjustable length to custom fit the person wearing the pillow, said flexible member comprising at least one strap which is affixed at a first end to one of the respective end portions of said first and second legs and which includes a releasable device affixed to a second end of said strap to connect said end portions of said first and second legs together, said releasable device which comprises respective releasably connectable first and second patches which are affixed to said second end portion of said strap and to another of the respective of said first and second legs, said first and second patches comprising one of a set of mating hook-and-loop fastener patches chosen from the group consisting of a hook patch and a loop patch.

4. The pillow of claim 3, wherein the body is of generally round cross-sections.

5. The pillow of claim 3, wherein the body is of generally rectangular cross-sections.

* * * * *